US009308399B2

(12) United States Patent
Zaidel et al.

(10) Patent No.: US 9,308,399 B2
(45) Date of Patent: Apr. 12, 2016

(54) TOOTH WHITENING COMPOSITION

(75) Inventors: Lynette Zaidel, Cranford, NJ (US);
Suman Chopra, Monroe, NJ (US);
Michael Prencipe, Princeton Junction, NJ (US); Prakasarao Mandadi, Flemington, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/582,115

(22) PCT Filed: Mar. 11, 2010

(86) PCT No.: PCT/US2010/026965
§ 371 (c)(1),
(2), (4) Date: Aug. 31, 2012

(87) PCT Pub. No.: WO2011/112193
PCT Pub. Date: Sep. 15, 2011

(65) Prior Publication Data
US 2012/0328535 A1    Dec. 27, 2012

(51) Int. Cl.
*A61Q 11/00* (2006.01)
*A61K 8/22* (2006.01)
*A61K 8/25* (2006.01)
*A61K 6/00* (2006.01)
*A61K 33/40* (2006.01)
*A61Q 11/02* (2006.01)
*A61K 8/31* (2006.01)
*A61K 8/49* (2006.01)
*A61K 8/81* (2006.01)
*A61K 8/891* (2006.01)

(52) U.S. Cl.
CPC . *A61Q 11/00* (2013.01); *A61K 8/22* (2013.01); *A61K 8/31* (2013.01); *A61K 8/4913* (2013.01); *A61K 8/8111* (2013.01); *A61K 8/8176* (2013.01); *A61K 8/891* (2013.01)

(58) Field of Classification Search
CPC ....... A61Q 11/00; A61K 8/22; A61K 8/8176; A61K 8/25; A61C 19/066
See application file for complete search history.

(56) References Cited

U.S. PATENT DOCUMENTS

| 3,376,110 | A | 4/1968 | Shiraeff |
| 3,480,557 | A | 11/1969 | Shiraeff |
| 5,122,370 | A | 6/1992 | Merianos et al. |
| 6,514,484 | B2 | 2/2003 | Rajaiah et al. |
| 6,860,736 | B2 | 3/2005 | Allred et al. |
| 7,011,523 | B2 | 3/2006 | Allred et al. |
| 7,323,161 | B2 | 1/2008 | Choi et al. |
| 2004/0219111 | A1 | 11/2004 | Kim et al. |
| 2004/0219190 | A1 | 11/2004 | Kosti |
| 2005/0031811 | A1 | 2/2005 | Mehan et al. |
| 2005/0036957 | A1 | 2/2005 | Prencipe et al. |
| 2005/0036959 | A1 | 2/2005 | Ibrahim et al. |
| 2005/0038181 | A1 | 2/2005 | Chopra et al. |
| 2005/0063923 | A1* | 3/2005 | Prencipe et al. ............... 424/53 |
| 2005/0069502 | A1 | 3/2005 | Chopra et al. |
| 2005/0186150 | A1 | 8/2005 | Allred et al. |
| 2005/0249678 | A1 | 11/2005 | Hassan et al. |
| 2006/0045854 | A1* | 3/2006 | Zaidel et al. ............... 424/53 |
| 2006/0142411 | A1 | 6/2006 | Ibrahim et al. |

FOREIGN PATENT DOCUMENTS

| WO | WO 2005/016299 | 2/2005 |
| WO | WO 2005/018593 | 3/2005 |
| WO | WO 2006/026424 | 3/2006 |
| WO | WO 2009/018593 | 2/2009 |

OTHER PUBLICATIONS

Camarco, Wayne. "Know your Vital Excipients." ISP Corp. Slide 10.*
International Search Report and Written Opinion of the ISA for corresponding International Application No. PCT/US2010/026965 mailed Feb. 7, 2011.

* cited by examiner

*Primary Examiner* — Robert A Wax
*Assistant Examiner* — Tracy Liu

(57) ABSTRACT

A tooth whitening composition for whitening a surface of a tooth, the composition comprising a mixture of a whitening agent comprising an aqueous peroxide, a hydrophobic polymer carrier for adhering the tooth whitening composition to a tooth surface and at least one adhesion enhancing agent.

10 Claims, No Drawings

TOOTH WHITENING COMPOSITION

BACKGROUND

It has become desirable for a person's teeth to appear bright or "white." Society places a high value on the "whiteness" of one's teeth. One whose teeth are white may enjoy more personal confidence and satisfaction and may even enjoy greater social acceptance.

In a mammal, a tooth is comprised of an inner dentin layer and an outer hard enamel layer that is the protective layer of the tooth. The enamel layer of a tooth is naturally an opaque white or slightly off-white color. It is the enamel layer that can become stained or discolored. The enamel layer of a tooth is composed of hydroxyapatite mineral crystals that create a somewhat porous surface. These hydroxyapatite crystals form microscopic hexagonal rods or prisms that make up the enamel surface. As a result, the surface of the enamel layer presents microscopic spaces or pores between the prisms. It is believed that this porous nature of the enamel layer is what allows staining agents and discoloring substances to permeate the enamel and discolor the tooth. These remaining substances can occupy the microscopic spaces and eventually alter the color of the tooth.

Many substances that a person confronts or comes in contact with on a daily basis can "stain" or reduce the "whiteness" of one's teeth. In particular, the foods, tobacco products and fluids that one consumes tend to stain one's teeth. These products or substances tend to accumulate on the enamel layer of the tooth and form a pellicle film over the teeth.

These staining and discoloring substances can then permeate the enamel layer. This problem occurs gradually over many years, but imparts a noticeable discoloration of the enamel of one's teeth. So long as the discolored teeth are still healthy and do not pose any health risk or problem, a product or substance that would whiten the discolored teeth would be advantageous. It is also essential that a tooth whitening product that is to be used at home or in private by the consumer be safe and easy to use and be stable and retain its whitening efficacy during its storage on retail store shelves as well as over the period of use by the consumer.

Products and substances that are presently available to whiten teeth include a variety of different ingredients, but the primary active ingredient is a peroxide agent formulated into an aqueous liquid, solution, paste or gel carrier. These products potentially lose their whitening efficacy over time as peroxide compounds in aqueous solutions are relatively unstable. This tendency toward instability of peroxide during storage has limited the utility of aqueous liquid whitening products for whitening teeth. It would be highly desirable, therefore, to provide a stable peroxide whitening liquid to effect substantive whitening.

In addition, there is a need to assist peroxide retention on the tooth surface to achieve the maximum bleaching performance. This may be achieved by incorporating the peroxide agent into an adhesive, for example a pressure sensitive adhesive that can adhere to the tooth surface.

International Patent Application Publication No. WO-A-2005/016299 discloses a silicone polymer-based tooth whitening composition in which a peroxide compound is dispersed in a hydrophobic silicone-based polymer.

U.S. Patent Application Publication No. 2005/0031811 discloses a silicone polymer-based liquid tooth whitening composition which is non-aqueous. An anhydrous peroxide compound is dispersed in a hydrophobic silicone-based pressure sensitive polymer.

U.S. Patent Application Publication No. 2005/0036959 discloses a composition for the rapid temporary whitening of teeth which comprises the combination of an adhesive material and hydroxyapatite. The adhesive material may be selected from natural resins, modified natural resins and pressure sensitive adhesives, for example polyvinylpyrollidione, polyvinylpyrollidione/vinyl acetate copolymers and polyethylene glycol.

U.S. Patent Application Publication No. 2006/0142411 discloses a composition for whitening teeth which comprises a whitening particulate comprising hydroxyapatite and a delivery system comprising a silicone resin and a silicone adhesive.

U.S. Pat. No. 7,011,523 discloses a solid composition for whitening teeth which comprises a whitening agent and a tooth adhesion agent that is substantially non-adhesive, or less adhesive, when the adhesive composition or layer is substantially solid but which becomes more adhesive to teeth when the adhesive composition or layer is moistened with water or saliva.

U.S. Pat. No. 6,860,736 discloses a composition for whitening teeth which comprises a whitening agent and a hydrophilic tissue adhesion agent.

U.S. Patent Application Publication No. 2005/0186150 discloses a dental bleaching device having a protective adhesive region that protects a person's gums from the dental bleaching composition during use. The dental bleaching composition includes a hydrophilic tissue adhesion agent.

U.S. Patent Application Publication No. 2005/0249678 discloses multilayer tooth whitening strips comprising a hydratable polymer and a whitening agent.

U.S. Patent Application Publication No. 2004/0219111 discloses a dry type adhesive device in which a peroxide tooth whitening agent is in an adhesive layer comprising a hydrophilic glassy polymer as a base polymer to provide adhesion to the teeth surface when hydrated U.S. Pat. No. 7,323,161 discloses a patch for whitening teeth which comprises a whitening agent and a tooth adhering layer containing hydrophilic erodable polymer complexes.

SUMMARY

There is a need in the art for improved tooth whitening compositions that can provide increased peroxide retention on the tooth surface and better whitening efficacy, as well as a stable formulation. In particular, it is a challenge in the art to retain peroxide on the tooth surface for a longer time.

There is also a need in the art for improved tooth whitening compositions that can provide a stable peroxide formulation, and for improved tooth whitening compositions that can provide peroxide release from the tooth whitening composition during the tooth whitening process which is closely matched with the peroxide retention on the tooth surface to achieve the maximum bleaching performance.

The present invention relates to tooth whitening compositions and in particular, such compositions comprising hydrophobic polymers and a whitening agent.

Accordingly, the present invention provides a tooth whitening composition for whitening a surface of a tooth, the composition comprising a mixture of a whitening agent comprising an aqueous peroxide, a hydrophobic polymer carrier for adhering the tooth whitening composition to a tooth surface, wherein the hydrophobic polymer is a silicone pressure sensitive adhesive, and at least one adhesion enhancing agent, the adhesion enhancing agent comprising a plastigel.

The present invention also provides a method for whitening a surface of a tooth in an oral cavity of a human or other animal subject which comprises (a) applying a tooth whitening composition of the present invention to the tooth surface to be whitened for a plurality of minutes per day; and (b) repeating step (a) for multiple days to thereby whiten the teeth.

The present invention also provides a method of whitening a tooth in a mammal, the method comprising applying to the tooth a tooth whitening composition comprising a mixture of a whitening agent comprising an aqueous peroxide, a hydrophobic polymer carrier for adhering the tooth whitening composition to a tooth surface, wherein the hydrophobic polymer is a silicone pressure sensitive adhesive, and at least one adhesion enhancing agent, the adhesion enhancing agent comprising a plastigel.

The applying may be achieved by contacting a film comprising the tooth whitening composition with the surface of the tooth, or by contacting a liquid form of the tooth whitening composition with the surface of the tooth.

DETAILED DESCRIPTION

The following definitions and non-limiting guidelines must be considered in reviewing the description of this invention set forth herein. The headings (such as "Background" and "Summary,") and sub-headings (such as "Compositions" and "Methods") used herein are intended only for general organization of topics within the disclosure of the invention, and are not intended to limit the disclosure of the invention or any aspect thereof. In particular, subject matter disclosed in the "Background" may include aspects of technology within the scope of the invention, and may not constitute a recitation of prior art. Subject matter disclosed in the "Summary" is not an exhaustive or complete disclosure of the entire scope of the invention or any embodiments thereof. Classification or discussion of a material within a section of this specification as having a particular utility (e.g., as being an "active" or a "carrier" ingredient) is made for convenience, and no inference should be drawn that the material must necessarily or solely function in accordance with its classification herein when it is used in any given composition.

The citation of references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features. Specific Examples are provided for illustrative purposes of how to make and use the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention. In addition, the compositions and the methods may comprise, consist essentially of, or consist of the elements described therein.

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material. The recitation of a specific value herein, whether referring to respective amounts of components, or other features of the embodiments, is intended to denote that value, plus or minus a degree of variability to account for errors in measurements. For example, an amount of 10% may include 9.5% or 10.5%, given the degree of error in measurement that will be appreciated and understood by those having ordinary skill in the art.

As referred to herein, "tooth" or "teeth" refers to natural mammalian teeth, dentures, dental plates, fillings, caps, crowns, bridges, dental implants, and the like, and any other hard surfaced dental prosthesis either permanently or temporarily fixed within the oral cavity. As used herein, "whitening" refers to a change in visual appearance of a tooth, preferably such that the tooth has a brighter shade.

Increase in whiteness of a dental surface can be observed visually, for example with the aid of color comparison charts or gauges, or measured by colorimetry, using any suiTable Instrument such as a Minolta Chromameter, e. g., model CR-400 (Minolta Corp., Ramsey, N.J.). The instrument can be programmed, for example, to measure Hunter Lab values or $L^*a^*b^*$ values according to the standard established by the International Committee of Illumination (CIE). The $L^*a^*b^*$ system provides a numerical representation of three-dimensional color space where $L^*$ represents a lightness axis, $a^*$ represents a red-green axis and $b^*$ represents a yellow-blue axis. The $L^*$ and $b^*$ axes are typically of greatest applicability to measurement of tooth whiteness. Increase in whiteness can be computed from differences in $L^*$, $a^*$ and $b^*$ values before and after treatment, or between untreated and treated surfaces. A useful parameter is $\Delta E^*$ calculated as the square root of the sum of the squares of differences in $L^*$, $a^*$ and $b^*$ values, using the formula: $\Delta E^* = [(\Delta L^*)^2 + (\Delta a^*)^2 + (\Delta b^*)^2]^{1/2}$.

A higher value of $\Delta E^*$ indicates greater increase in whiteness. In various embodiments, the method of the present invention can effect $\Delta E^*$ of at least 3, or at least 4, or at least 5, or at least 10.

It has been discovered that compositions and methods of this invention afford advantages over whitening compositions among those known in the art including one or more of: enhanced whitening efficacy, providing a higher available concentration of whitening agent, stability of the whitening agent during storage, adherence of the whitening composition to the tooth surface even in the presence of saliva and sustained and controlled delivery of the whitening agent for a longer duration of time. Further uses, benefits and embodiments of the present invention are apparent from the description set forth herein.

In particular, while not intending on being bound by any theory of operability, the present inventors believe that hydrophobic adhesives (such as silicone resin, silicone adhesives, etc.) which are substantive to, and can be readily adhered to, the tooth surface, surprisingly can be combined with an aqueous peroxide, such as hydrogen peroxide, and adhesion enhancing agents including a plastigel to form a stable, highly retentive and efficacious tooth whitening gel. This was despite the expectation that the hydrophobic adhesives could not be compatible with aqueous ingredients.

Tooth Whitening System

In various embodiments, the present invention provides an improved tooth whitening system that employs a tooth whitening composition that adheres to a surface of a tooth to be whitened. The tooth whitening composition comprises an aqueous peroxide whitening agent and a hydrophobic polymer carrier in combination with a plastigel.

In various embodiments, the hydrophobic polymer carrier of the whitening composition provides a stable vehicle or carrier for the whitening agent during storage and before use. The whitening composition will gradually dissolve or disintegrate upon exposure to the saliva in the aqueous oral cavity environment, thus providing delivery of the whitening agent to a tooth surface. In some embodiments, it is preferred that the hydrophobic polymer carrier is non-water soluble and thus is stable for longer durations during exposure to saliva and other aqueous solutions found in an oral cavity, as compared to prior art water-soluble hydrophilic carriers.

In various embodiments, the whitening composition can be incorporated into a dental strip or film form, or into a liquid product which can be applied to the surface of a tooth by manual application. Upon application to the surface of a tooth, the applied whitening composition forms an adherent layer of whitening agent containing product that has the capacity to release the whitening agent over an extended period of time, e. g., from 5 to 45 minutes. The applied layer adheres to the tooth surface and the released whitening agent effects whitening of the tooth surface to which the composition is applied.

In another embodiment, methods of whitening a surface of a tooth are provided.

Whitening Compositions

The present invention provides a whitening composition for use in a tooth whitening system. In one embodiment, the whitening composition comprises an aqueous peroxide whitening agent and a hydrophobic polymer carrier (preferably a silicone pressure sensitive adhesive) in combination with a plastigel as an adhesion enhancing agent. The whitening composition may further comprise other additional ingredients that include those known to one of skill in the art, including one or more of the following components: surfactants, flavoring agents, sweeteners, desensitizing agents, antimicrobial agents, anti-caries agents, anti-calculus agents, anti-inflammatory agents, vitamins, pigments and coloring agents, and enzymes, as will be discussed in greater detail below.

Active ingredients useful herein are optionally present in the compositions of the present invention in safe and effective amounts. A "safe and effective" amount of an active is an amount that is sufficient to have the desired therapeutic or prophylactic effect in the human or lower animal subject to whom the active is administered, without undue adverse side effects (such as toxicity, irritation, or allergic response), commensurate with a reasonable benefit/risk ratio when used in the manner of this invention.

The specific safe and effective amount of the active will vary with such factors as the particular condition being treated, the physical condition of the subject, the nature of concurrent therapy (if any), the specific active used, the specific dosage form, the carrier employed, and the desired dosage regimen.

In some embodiments, the silicone pressure sensitive adhesive comprises from 5 to 35 weight % of the composition and the plastigel comprises from 30 to 60 weight % of the composition.

The composition may further comprise crospovidone as an adhesion enhancing agent. The composition may comprise from 10 to 20 weight % of the crospovidone. The whitening composition may comprise from 0.1 to 50 weight % of the aqueous peroxide.

The aqueous peroxide may comprise hydrogen peroxide. The hydrogen peroxide may be present in an amount of from 0.035 to 17.5 weight % hydrogen peroxide, optionally in an amount of from 3 to 10 weight % hydrogen peroxide. The whitening composition may have a viscosity of from 10,000 to 900,000 cps., as measured on Brookfield viscometer at 25° C., using spindle E.

The whitening composition may further comprise one or more of the following components: a surfactant, a flavoring agent, a desensitizing agent, an antimicrobial agent, an anti-caries agent, and an anti-calculus agent.

In one embodiment, the whitening composition comprises from 5 to 35 weight % of silicone pressure sensitive adhesive, from 0.1 to 50 weight % of aqueous peroxide, from 30 to 60 weight % of the plastigel adhesive enhancing agent; and from 0 to 1 weight % of at least one of a flavoring agent and a sweetening agent.

Whitening Agents

In various embodiments, the compositions of the present invention comprise an aqueous peroxide whitening agent as the main active ingredient. As further discussed below, a "whitening agent" is a material which effects whitening of a tooth surface to which it is applied.

In various embodiments, the whitening agent comprises a peroxide compound. As referred to herein, a "peroxide compound" is an oxidizing compound comprising a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxy phthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound comprises hydrogen peroxide, urea peroxide, sodium percarbonate and mixtures thereof.

Peroxide releasing compounds particularly useful in the whitening compositions of the present invention include peroxide containing compounds such as urea peroxide, sodium percarbonate, sodium perborate and polyvinylpyrrolidone-$H_2O_2$ complexes (hereinafter "PVP-$H_2O_2$"). Polyvinylpyrrolidone is also known as poly-N-vinyl-poly-2-pyrrolidone and commonly abbreviated to "PVP". PVP generally refers to a polymer containing vinylpyrrolidone (also referred to as N-vinylpyrrolidone, N-vinyl-2-pyrrolidione and N-vinyl-2-pyrrolidinone) as a monomeric unit. The monomeric unit consists of a polar imide group, four non-polar methylene groups and a non-polar methane group.

Both linear and cross-linked complexes of PVP-$H_2O_2$ are known in the art and are disclosed in U.S. Pat. No. 3,376,110, U.S. Pat. No. 3,480,557 and U.S. Pat. No. 5,122,370. PVP-$H_2O_2$ is sTable ln an anhydrous environment. Upon exposure to highly aqueous environments, such as in the oral cavity, the PVP-$H_2O_2$ dissociates into individual species (PVP polymer and $H_2O_2$). In one embodiment, the PVP-$H_2O_2$ complex is 80% by weight polyvinylpyrrolidone and 20% by weight $H_2O_2$.

In alternate embodiments, the whitening agent comprises a liquid peroxide solution. The hydrophobic polymer carrier of the whitening composition provides sufficient stability to permit the use of a liquid hydrogen peroxide. The liquid hydrogen peroxide comprises $H_2O_2$ generally contained in an aqueous water-based solution. In some embodiments, the liquid hydrogen peroxide has a concentration of peroxide to the total solution of 0.035 to 17.5%, more preferably 3 to 10% by weight, which for example may be achieved by adding a 35 wt % aqueous $H_2O_2$ solution at a concentration of from 0.1 to 50 wt %, more preferably 8 to 29% by weight, typically from 15 to 25 wt %. Additionally, a stabilizer may be present. For example, a 3% hydrogen peroxide solution with 0.1 to 0.5% of a stabilizer may be used. Acetanilide or a similar organic material can also be used with a pyrophosphate stabilizer such as sodium acid pyrophosphate (0.1 to 1.0%) with a preferred amount of 0.5%.

In certain embodiments, an agent to enhance release of the peroxide in the oral cavity is present as a part of the peroxide component whitening agent. Polypore, which is an allyl methacrylate crosspolymer, available from Amcol health & Beauty Solutions, Inc., is such an enhancing agent.

In various embodiments, the aqueous peroxide whitening, agent of the whitening composition comprises from 0.1% to 50%, optionally from 0.5% to 50%, and optionally from 10% to 40% of the oral care composition.

Hydrophobic Polymer Carrier

The present invention preferably comprises a carrier that comprises a hydrophobic polymer. The term "hydrophobic" or "water-insoluble" as applied to polymers and as employed herein refers to an organic polymer which is substantially non-aqueous having a water solubility of less than one gram per 100 grams of water at 25° C. In various embodiments, a hydrophobic polymer is compatible with the whitening agents previously described above. In certain embodiments, a hydrophobic polymer is selected for the carrier to produce a tooth whitening composition having a viscosity of from 1,000 centipoise (cP) to 900,000 cP, preferably greater than 10,000 cP and less than 900,000 cP more preferably greater than 10,000 cP and less than 100,000 cP.

One preferred class of hydrophobic polymers comprise siloxane polymers. which are also generally known in the art as "silicone" polymers, and preferably are silicone pressure sensitive adhesives. In certain embodiments of the present invention, the hydrophobic polymers in the carrier are those in which a whitening agent can be dispersed and are well known in the art. Many such silicone polymers are commercially available.

In various embodiments, a preferred silicone-based hydrophobic polymer is a polyorganosiloxane. One such polyorganosiloxane is produced by condensing a silicone resin and an organosiloxane such as a polydiorganosiloxane. Such hydrophobic polymers are an elastomeric, tacky material, adhesion of which to dental enamel surfaces can be varied by altering the ratio of silicone resin to polydiorganosiloxane in the copolymer molecule. Preferably, the polymers are pressure sensitive hydrophobic polymers specifically designed for pharmaceutical use and are permeable to many drug compounds and find application for the transdermal application of various compounds. In one such embodiment, the silicone polymers are the copolymer product of mixing a silanol terminated polydiorganosiloxane such as polydimethyl siloxane with a silanol-containing silicone resin whereby the silanol groups of the polydiorganosiloxane undergo a condensation reaction with the silanol groups of the silicone resin so that the polydiorganosiloxane is lightly crosslinked by the silicone resin (that is, the polydiorganosiloxane chains are bonded together through the resin molecules to give chain branching and entanglement and/or a small amount of network character) to form the silicone hydrophobic polymers. A catalyst, for example, an alkaline material, such as ammonia, ammonium hydroxide or ammonium carbonate, can be mixed with the silanol-terminated polydiorganosiloxane and the silicone resin to promote this crosslinking reaction. By copolymerizing the silicone resin with the silanol terminated polydiorganosiloxane, there results a polymer with self adhering properties and the cohesive properties of a soft elastomer matrix characteristic of pressure sensitive polymers being distinguished from the hard, non-elastomeric properties of other silicone resins. In one embodiment, hydrophobic polymers used in the carrier are available from the Dow-Corning Company under the brand name BIO-PSA.

The modification of a ratio of silicone resin to polydiorganosiloxane modifies the tackiness of the hydrophilic polymer. This ratio can be in the range of 70:30 to 50:50. For example, the BIO-PSA silicone sold by Dow-Corning is available in three silicone resin to silicone polymer ratios namely, 65/35 (low tack), 60/40 (medium tack), 55/45 (high tack). Such a polyorganosiloxane pressure sensitive adhesive is available dissolved in either ethyl acetate solvent or dimethicone.

In various embodiments, the hydrophobic polymer carrier is preferably present in the liquid whitening compositions of the present invention at a concentration of from 5 to 50% (by weight), optionally from 10% to 35%.

Adhesion Enhancing Agents

In one embodiment of the present invention, the whitening composition further comprises at least one adhesion enhancing agent that augments adhesion of the whitening composition to the surface of the tooth, i. e. adhesion to the enamel. Adhesion enhancing agents useful with the present invention include inorganic materials as well as organic natural and synthetic polymers. Inorganic materials include amorphous silica compounds which function as thickening agents, and include colloidal silica compounds available under trademarks such as Cab-o-sil fumed silica manufactured by Cabot Corporation and distributed by Lenape Chemical, bound Brook, N.J.: Zeodent 165 from J. M. Huber Chemicals Division, Havre de Grace, Md. 21078; and Sylox 15 also known as Sylodent 15, available from Davison Chemical Division of W. R. Grace Corporation, Baltimore, Md. 21203.

In certain embodiments, the inorganic adhesion enhancing material, such as silica, is surface treated to compatibilize the adhesion enhancing agent with the hydrophobic components in the whitening composition.

Organic materials which may be included in the compositions of the present invention to enhance the properties of the hydrophobic polymers of the present invention include adhesion enhancing agents such as waxes, inclusive of beeswax, mineral oil, plastigel (a blend of mineral oil and polyethylene), petrolatum, white petrolatum, shellac, versagel (blend of liquid paraffin, butene/ethylene/styrene hydrogenated copolymer), polyethylene waxes, microcrystalline waxes, polyisobutene, polyvinylpyrrolidone/vinyl acetate copolymers, and insoluble polyacrylate copolymers. One particularly preferred adhesion enhancing material is a plastigel sold under the trade name Plastigel 5, available in commerce from Lyne Laboratories, Brockton, Mass. USA. The plastigel is preferably in an amount of from 20 to 70 weight %, more preferably from 30 to 60 weight %, based on the weight of the composition.

The compositions of the present invention may further comprise crospovidone (poly[N-vinyl-2-pyrrolidone]) as an adhesion enhancing agent, preferably in an amount of from 10 to 20 weight % based on the weight of the composition.

Also effective as adhesion enhancing agents are liquid hydrophilic polymers including polyethylene glycols, non-ionic polymers of ethylene oxide having the general formula: $HOCH_2(CH_2OCH_2)_nCH_2OH$ wherein n represents the average number of oxyethylene groups. Polyethylene glycols available from Dow Chemical are designated by a number such as 200, 300, 400, 600, and 2000, which represents the approximate average molecular weight of the polymer, as well as nonionic block copolymer of ethylene oxide and propylene oxide of the formulas:

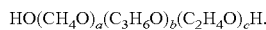

$$HO(CH_4O)_a(C_3H_6O)_b(C_2H_4O)_cH.$$

The block copolymer is preferably chosen (with respect to a, b and c) such that the ethylene oxide constituent comprises from 65 to 75% by weight, of the copolymer molecule and the copolymer has an average molecular weight of from 2,000 to 15,000 with the copolymer being present in the liquid tooth whitening composition in such concentration that the composition is liquid at room temperature (23° C.).

A particularly desirable block copolymer for use in the practice of the present invention is available commercially from BASF and designated Pluraflo L1220 which has an average molecular weight of 9,800. The hydrophilic poly(ethylene oxide) block averages 65% by weight of the polymer.

Adhesion enhancing agents employed in compositions of various embodiments of the invention are present in an amount of from 10 to 80% by weight. Preferably, the adhesion enhancing agents are present in an amount of from 30 to 75% by weight.

Additional Components

As previously described, many other components may further be included in the whitening compositions of the present invention, and include flavouring agents, sweetening agents, surfactants, anti-microbial agents, anti-inflammatory agents, plaque buffers, vitamins, anti-caries agents, anti-plaque agents, desensitizing agents, coloring agents, pigments and pacifying agents, for example.

In certain embodiments, nonionic surfactants are present in the whitening composition. These surfactants are preferably compatible with the whitening agents and serve as solubilizing, dispersing, emulsifying and wetting agents. In one aspect, surfactants are especially effective to solubilize a flavoring agent, if flavor is desired for the liquid whitening composition. A particularly useful nonionic surfactant is a water soluble polyoxyethylene monoester of sorbitol with a $C_{10}$ to $C_{18}$ fatty acid, marketed commercially under the TWEEN® trademark. The TWEEN surfactants are mixtures of $C_{10}$ to $C_{18}$ fatty acid esters of sorbitol (and sorbitol anhydrides), consisting predominately of the monoester, condensed with 10-30, preferably 20, moles of ethylene oxide. The fatty acid (aliphatic hydrocarbonyl monocarboxylic acid) may be saturated or unsaturated, e.g. lauric, palmitic, stearic, oleic acids. Polysorbate 20 (e.g. TWEN 20) is especially preferred and is commonly referred to as polyoxyethylene (20) sorbitan monolaurate. The nonionic surfactant constitutes 0 to 50% by weight and preferably 0.5 to 40% by weight of the liquid composition.

In an embodiment where the whitening composition has a flavoring agent, the flavoring agent is selected from essential oils, as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint, spearmint and wintergreen. The flavoring agent is preferably incorporated in the whitening composition of the present embodiment at a concentration of 0 to 2% by weight and more preferably 0.1 to 0.5% by weight.

In embodiments where the whitening composition is sweetened, a sweetening material is used as an alternative or complement to the flavoring agent. Suitable sweetening agents are water-soluble and include sodium saccharin, sodium cyclamate, xylitol, perillartien, D-tryptophan, aspartame, dihydrochalcones and the like, in concentrations of 0.01 to 1% by weight. Sodium saccharin is preferred.

Other ingredients which are included in various embodiments of the liquid whitening composition comprise materials commonly used in the oral care formulations.

These include: antimicrobial agents, e. g. Triclosan, chlorhexidine, copper-, zinc- and stannous salts such as zinc citrate, zinc sulfate, zinc glycinate, sodium zinc citrate and stannous pyrophosphate, sanguinarine extract, metronidazole, quaternary ammonium compounds, such as cetylpyridinium chloride; bis-guanides, such as chlorhexidine digluconate, hexetidine, octenidine, alexidine; and halogenated bisphenolic compounds, such as 2,2'methylenebis-(4-chloro-6-bromophenol); anti-inflammatory agents such as ibuprofen, flurbiprofen, aspirin, indomethacine; anti-caries agents such as sodium-, calcium-, magnesium- and stannous fluoride, aminefluorides, disodium monofluorophosphate and sodium trimetaphosphate; plaque buffers such as urea, calcium lactate, calcium glycerophosphate and strontium polyacrylates; vitamins such as Vitamin C; plant extracts; desensitizing agents, e. g., potassium citrate, potassium chloride, potassium tartrate, potassium bicarbonate, potassium oxalate, potassium nitrate and strontium salts; agents effective against dental calculus such as pyrophosphate salts including the mono, di, tri and tetra alkali metal and ammonium pyrophosphate and tripolyphosphate salts; biomolecules, e. g., bacteriocins, antibodies, enzymes such as papain, glucoamylase; opacifying agents, pigments, coloring agents and fluoride ion providing salts having anti-caries efficacy such as sodium fluoride, potassium fluoride, a tin fluoride such as stannous fluoride. In another embodiment, the whitening composition comprises one or more desensitizing agents, such as potassium nitrate, citric acid, citric acid salts, strontium chloride and the like.

The whitening composition of the present invention may be in the form of a layer of a strip prepared using a conventional solvent casting process. Strips among those useful herein comprise polymers, natural and synthetic woven materials, non-woven material, foil, paper, rubber and combinations thereof. Preferably the strip of material is substantially water insoluble. Suitable polymers include polyethylene, ethylvinylacetate, polyesters, ethylvinyl alcohol, fluoroplastics, and combinations thereof. In various embodiments, the strip of material is generally 1 mm thick, or less than 1 mm thick, optionally less than 0.05 mm thick, optionally 0.001 to 0.03 mm thick. The shape of the strip is any shape and size that covers the desired oral surface. In one embodiment, the length of the strip material is from 2 cm (centimeter) to 12 cm, in another embodiment from 4 cm to 9 cm. The width of the strip material will also depend on the oral surface area to be covered. The width of the strip is generally from 0.5 cm to 4 cm, in one embodiment from 1 cm to 2 cm. The strip material may comprise shallow pockets, optionally filled by a composition of this invention. Strips among those useful herein are disclosed in U.S. Pat. No. 6,514,484 of Rajaiah et al.

For example, in some embodiments, a strip is prepared by solvent casting, an adhesive polymer or resin such as colophonium and/or polyvinylpyrrolidone is dissolved in a sufficient amount of a compatible solvent such as ethanol. After a solution has been formed, the addition of the base whitening composition follows and any other ingredients such as sweeteners or flavors. The solution is coated onto a suitable casting carrier material from which the formed strip can be easily released from without damage. The carrier material must have a surface tension which allows the solution to spread evenly across the intended carrier width without soaking in to form a destructive bond between the two substrates.

Examples of suitable carrier materials include glass, stainless steel, teflon, polyethylene impregnated kraft paper. The strip may be dried to a solid usable form in a high temperature air bath using a drying oven, drying tunnel, vacuum drier, or any other suitable drying equipment at a temperature. Thereafter the strip formed on the carrier is peeled off the carrier surface and cut into pieces of suitable size and shape for consumer use and packed into a suitable container.

To use the whitening strip for the present invention, the strip when applied to the teeth surface will adhere to the teeth in an appropriate manner and within 1 to 60 minutes, the teeth surfaces will whiten to a natural appearance as the whitening agent (s) present in the strip matrix migrate to the tooth surfaces. The composition can be applied to the tooth surface to be whitened for a plurality of minutes per day. The application of the composition can be repeated for multiple days to thereby whiten the teeth.

In this regard, the whitening strip is formed to have a width dimension suitable to cover one or more teeth in a row (upper or lower). Therefore, the whitening strip may be applied to one or more of the upper set of teeth, or to one or more of the lower set of teeth either separately or simultaneously. The length dimension of the whitening strip is determined by the amount of coverage desired. In this regard, the number of teeth which it is desired to whiten will determine the dimensions for the whitening strip. For instance, it may be desired to only whiten the front teeth, which are most easily seen by others. Accordingly, the length of whitening strip can be reduced in this case, as compared to the case where it is desired to whiten all of the teeth. The duration of application of whitening strip to the teeth will depend upon the type and concentration of the whitening agent (s), as well as the type and intensity of stain. After the teeth are whitened to the satisfaction of the user, the portions of the strip can be easily removed by rinsing the mouth with water and brushing.

In one preferred embodiment, the whitening composition is applied using a "paint-on" technique. A small application device, such as a brush or spatula is coated with a composition of this invention and the composition is then placed on a tooth surface. Preferably, the composition is spread evenly on such surfaces, in sufficient quantity to deliver whitening agent (s) to the stained surfaces.

The paint-on whitening composition of the present invention is prepared in the form of a flowable viscous liquid suspension containing the whitening agent and is applied as such to the subject's teeth, by manual application, such as by painting the teeth with a soft applicator brush in the same manner as application of nail polish to a. finger nail and without the intervention of a dentist or technological operations. Application by the user and evaporation or dissolution of the solvent leaves an adherent natural appearing white coating on the teeth. In various embodiments, the layer of tooth whitening composition applied to tooth enamel contains no ingredients imparting thereto an unacceptable taste or texture, rendering it unpleasant to the user while adhering strongly to tooth enamel. The composition is sufficiently adherent to tooth enamel to remain on the teeth for the applied whitening composition enabling the applied coating to resist the forces commonly applied by the lips and tongue as well a those forces encountered during normal mastication, as upon the evaporation or dissolution of the solvent in mouth after application a hard coating of whitening composition forms in 1 minute which coating is bonded securely to the tooth enamel to which it is applied. While the layer of applied paint-on whitening composition is in place, the user is to refrain from mastication. The whitening composition can be removed as and when required, at will, by an employment of standard oral hygiene procedures such as brushing or by rinsing with an alcoholic mouthwash.

Methods

In one embodiment, the present invention provides a method of whitening the surface of a tooth in the oral cavity of a human or other animal subject using a tooth whitening composition comprising a whitening agent and a hydrophobic polymer carrier, preferably a silicone pressure sensitive adhesive, and an adhesion enhancing agent, preferably a plastigel.

The method comprises contacting the composition with the surface of the tooth. The contacting occurs for a duration of time sufficient to satisfactorily effect whitening of the teeth. Thus, the contacting occurs for a sufficient period of time to at least partially whiten teeth. This can be a period of time from 1 minute to 2 hours or longer. In certain embodiments, the contacting is for a period of time from 1 minute to 5 minutes, 1 minute to 45 minutes, 5 minutes to 45 minutes, or 5 minutes to 30 minutes.

The substantially non-aqueous tooth whitening composition is effective over a longer period of time, since it is not significantly diluted washed away in the oral cavity during the treatment time.

In another embodiment of the present invention, a method is provided for whitening a surface of a tooth in an oral cavity of a human or other animal subject which comprises preparing a liquid tooth whitening composition as previously described. The composition is applied to the tooth surface to be whitened for one or a plurality of minutes per day. The application then is repeated for multiple days to expose the teeth to multiple doses of whitening agent, and thus, thereby whitens the surface of the tooth.

The liquid whitening compositions of the present invention may be prepared by adding and mixing the ingredients of the composition in a suitable vessel such as a stainless steel tank provided with a mixer. In the preparation of the liquid whitening composition, the ingredients are advantageously added to the mixer in the following order: liquid anhydrous silicone based pressure sensitive polymer (hydrophobic polymer carrier), peroxide whitening agent, adhesion enhancing agent and any desired flavoring or sweetener. The ingredients are then mixed to form a homogeneous dispersion/solution.

The present invention is illustrated by the following non-limiting Examples.

SPECIFIC EMBODIMENTS OF THE INVENTION

Experimental Example

Examples 1 to 5 and Comparative Examples 1 and 2

A series of liquid whitening paint-on compositions was prepared using the ingredients listed in Table 1 below for Examples 1 to 5. These compositions incorporated aqueous hydrogen peroxide solution (as a 35 wt % aqueous solution of H$_2$O$_2$) into a hydrophobic silicone polymer carrier.

The whitening compositions of the Examples were prepared by mixing the pressure sensitive adhesive BIO-PSA and crospovidone, when present, for 10 minutes at high speed under vacuum. Hydrogen peroxide and sweetener were added and mixed under vacuum for 10 minutes, followed by Plastigel 5 adhesion enhancing agent, when present, and flavor and sodium saccharin, when present, were added and the mixture mixed for an additional 10 minutes.

The composition of Comparative Example 1 is also shown in Table 1, which did not include the BIO-PSA adhesive, but included Plastigel 5 and crospovidone together with the hydrogen peroxide, flavour and sodium saccharin.

Peroxide Stability

The compositions of these Examples were found to be stable with respect to the hydrogen peroxide. For example, the composition of Example 1 was subjected to an accelerated aging test by being held at a temperature of 105° F. for a period of eight weeks. The composition was physically stable and retained more than 90 weight % of the initial peroxide level. The composition had a good consistency and was easy to apply to the teeth by brushing.

Peroxide Retention

The in vitro retention of some of the compositions of the Examples, in particular Examples 1 to 3, and of Comparative Example 1, when applied as a film on human extracted teeth, was measured using an ultrasonic model. As a further Comparative Example 2, an aqueous hydrogen peroxide composition not containing a film-forming polymer, was employed as a control composition, designated as Comparative Example 2. The relationship between the % peroxide retained and time is shown in Table 3 for Examples 1 to 3 and the Comparative Examples 1 and 2.

It may be seen that the composition of Comparative Example 1 containing a film-forming polymer (Plastigel 5) showed increased peroxide retention as compared to the Control composition C of the Comparative Example 2. In the compositions of Examples 1 to 3, the peroxide retention was increased even further as compared to the composition of Comparative Example 1 due to the addition of the silicone pressure sensitive adhesive (Bio-PSA) to the composition. As the total amount of hydrophobic polymer, acting as adhesive, was increased in the compositions to above 10 wt % in Examples 1 to 3, the peroxide retention also increased.

The crospovidone was incorporated into the compositions of some of the Examples to adjust the viscosity of the composition and to act as an adhesion enhancing agent and therefore provide additional adhesion of the film to the tooth surface.

Whitening Efficacy

The compositions of Example 1 and of Comparative Examples 1 and 2 were subjected to an in vitro whitening efficacy test. The results are shown in Table 2.

The in vitro whitening efficacy was determined using a duplicate pair of flow cells designed to accommodate a total of eight bovine enamel blocks (four in each cell). The bovine enamel blocks were obtained freshly stained using an established staining protocol developed by Indiana University, Indianapolis, Ind. Then all surface stain was removed with prophylaxis paste. The initial carried L*, a* and b* matched as closely as possible prior to the experiment using a chromameter (Minolta CR-321) based on initial L*, a* and b* values (CIELAB). These initial values were typically L*=25.00, a*=3.00 and b*=5.00 to L*=35.00, a*=5.00 and b*=7.00. The L, a, b values were measured four times at slightly different locations on the surface of the bovine enamel blocks. To simulate the saliva of the human mouth, an artificial saliva buffer solution maintained at 37° C. was prepared which contained the salts usually present in saliva at levels typical to the levels found in human saliva. The bovine enamel blocks were placed in the flow cells and the compositions evenly applied using a brush, the amount of product applied being determined using the weight difference of the container. Flow over the teeth was 0.6 ml/min for 30 minutes. Average initial and final chromameter readings were used to calculate ΔE according to the formula: $\Delta E=[(\Delta L)^2+(\Delta a)^2+(\Delta b)^2]^{1/2}$. The process was repeated for a total of eight 30 minute treatments. The final ΔE reported was the average over all observations after the rejection of statistical outliers using the Student's test (95% confidence level).

The results of Table 2 show significantly increased whitening efficacy for Example 1 as compared to Comparative Examples 1 and 2. In particular, Example 1 shows significantly increased whitening efficacy as compared to Comparative Example 1, which is believed to result from the increased retention on the tooth surface due to the BIO-PSA adhesive added to the plastigel.

TABLE 1

| Ingredients | Comp. Ex. 1 | Comp. Ex. 2 | Ex. 1 | Ex. 2 | Ex. 3 | Ex. 4 | Ex. 5 |
| --- | --- | --- | --- | --- | --- | --- | --- |
| BIO-PSA * | 0 | 0 | 30 | 15 | 10 | 30 | 30 |
| Plastigel 5 | 67.24 | 0 | 37.24 | 52.24 | 57.24 | 52.2 | 34.1 |
| 35 wt % hydrogen peroxide | 16.86 | 51.47 | 16.86 | 16.86 | 16.86 | 16.9 | 25 |
| Sodium saccharin | 0.3 | 0.92 | 0.3 | 0.3 | 0.3 | 0.3 | 0.3 |
| Mint flavor | 0.6 | 1.83 | 0.6 | 0.6 | 0.6 | 0.6 | 0.6 |
| Crospovidone | 15 | 45.79 | 15 | 15 | 15 | 0 | 10 |
| Total (wt %) | 100 | 100 | 100 | 100 | 100 | 100 | 100 |

TABLE 2

|  | ΔE |
| --- | --- |
| Comparative Example 2 | 2.0 |
| Comparative Example 1 | 4.5 |
| Example 1 | 10.3 |

TABLE 3

| | In vitro peroxide retention on tooth surface, % | | | | |
|---|---|---|---|---|---|
| Time (min) | Comp. Ex. 1 | Comp. Ex. 2 | Ex. 1 | Ex. 2 | Ex. 3 |
| 0 | 100 | 100 | 100 | 100 | 100 |
| 1 |  | 44 |  |  |  |
| 5 |  | 8 |  |  |  |
| 15 | 36 |  | 74 | 81 | 80 |
| 30 | 28 |  | 60 | 67 | 55 |
| 60 |  |  | 52 | 60 | 32 |

We claim:

1. A tooth whitening composition for whitening a surface of a tooth, the composition comprising:
   a) a whitening agent comprising an aqueous peroxide,
   b) a hydrophobic polymer carrier for adhering the tooth whitening composition to a tooth surface, wherein the hydrophobic polymer is a silicone pressure sensitive adhesive, and
   c) at least one adhesion enhancing agent;
   wherein the tooth whitening composition comprises from 5 to 50 weight % of said silicone pressure sensitive adhesive;
   wherein said tooth whitening composition comprises from 30 to 60% weight % of said composition of plastigel and from 10 to 20 weight % of said composition of crospovidone as an adhesion enhancing agent, the plastigel comprising a blend of mineral oil and polyethylene;
   wherein the aqueous peroxide comprises hydrogen peroxide in an amount of from 0.01 to 17.5 weight % hydrogen peroxide by weight of the tooth whitening composition.

2. The composition according to claim 1, wherein the tooth whitening composition comprises from 0.1 to 50 weight % of said aqueous peroxide.

3. The composition according to claim 1, wherein the hydrogen peroxide is present in an amount of from 3 to 10 weight %.

4. The composition according to claim 1, wherein the tooth whitening composition has a viscosity of from 10,000 to 900,000 cps., measured on a Brookfield Viscometer at 25° C., spindle E.

5. The composition according to claim 4, wherein the tooth whitening composition further comprises one or more of the following components: a surfactant, a flavoring agent, a desensitizing agent, an antimicrobial agent, an anti-caries agent, and an anti-calculus agent.

6. The composition according to claim 4, wherein the tooth whitening composition further comprises from 0 to 1 weight % of at least one of a flavoring agent and a sweetening agent.

7. A method for whitening a surface of a tooth in an oral cavity of a mammal comprising:
   a) applying the tooth whitening composition of claim 1 to the tooth surface to be whitened for a plurality of minutes per day; and
   b) repeating (a) for multiple days to thereby whiten the teeth.

8. The method according to claim 7, wherein applying is achieved by contacting a film comprising the tooth whitening composition with the surface of the tooth.

9. The method according to claim 7, wherein applying is achieved by contacting a liquid form of the tooth whitening composition with the surface of the tooth.

10. The composition according to claim 1, wherein the adhesion enhancing agent is configured to form a film on a tooth surface to retain at least 52% of the hydrogen peroxide on the tooth surface for up to 60 minutes after application.

* * * * *